US012611433B2

(12) United States Patent
Xu et al.

(10) Patent No.: US 12,611,433 B2
(45) Date of Patent: Apr. 28, 2026

(54) *ANAEROSTIPES* SP B2131 STRAIN AND APPLICATION THEREOF IN INFLAMMATORY BOWEL DISEASES

(71) Applicant: Zhejiang university, Hangzhou (CN)

(72) Inventors: Zhengping Xu, Hangzhou (CN); Desen Sun, Hangzhou (CN); Jinghao Sheng, Hangzhou (CN); Rongpan Bai, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 925 days.

(21) Appl. No.: 17/595,831

(22) PCT Filed: Jan. 8, 2021

(86) PCT No.: PCT/CN2021/070872

§ 371 (c)(1),
(2) Date: Nov. 24, 2021

(87) PCT Pub. No.: WO2021/143621

PCT Pub. Date: Jul. 22, 2021

(65) Prior Publication Data

US 2025/0262252 A1      Aug. 21, 2025

(30) Foreign Application Priority Data

Jan. 13, 2020    (CN) ......................... 202010033957.1

(51) Int. Cl.
*A61K 35/742*        (2015.01)
*A61K 9/00*          (2006.01)
*A61P 1/00*          (2006.01)
*C12N 1/20*          (2006.01)
*C12N 1/205*         (2026.01)
*C12R 1/01*          (2006.01)

(52) U.S. Cl.
CPC .......... *A61K 35/742* (2013.01); *A61K 9/0053* (2013.01); *A61P 1/00* (2018.01); *C12N 1/205* (2021.05); *C12R 2001/01* (2021.05)

(58) Field of Classification Search
None
See application file for complete search history.

(56) References Cited

FOREIGN PATENT DOCUMENTS

| | | |
|---|---|---|
| CN | 108712906 A | 10/2018 |
| CN | 111117925 A | 5/2020 |
| WO | 2017223273 A1 | 12/2017 |
| WO | 2018107365 A1 | 6/2018 |
| WO | 2020005995 A2 | 1/2020 |

OTHER PUBLICATIONS

ISR of PCT/CN2021/070872.

*Primary Examiner* — Brian Gangle
(74) *Attorney, Agent, or Firm* — Hemisphere Law, PLLC

(57)        ABSTRACT

Provided are an *Anaerostipes* sp. B2131 strain and an application thereof in inflammatory bowel diseases. The *Anaerostipes* sp. B2131 strain has a deposit number of CGMCC NO. 1.5.5295. The *Anaerostipes* sp. B2131 strain is used for regulating the homeostasis of intestinal flora, and preventing and treating the occurrence of an intestinal disease such as an inflammatory bowel disease.

13 Claims, 4 Drawing Sheets

Specification includes a Sequence Listing.

A

*Anadrostipes sp. B2131* strain 16S rDNA partial sequence tgggtcactgacttcgggcgttactgactcccatggtgtgacgggcggtgtgtacaagacccgggaacgtattcaccgcgacattctgattcgcgattactagcgattccagctt catgtagtcgagttgcagactacaatccgaactgagacgttatttttgggatttgctcactctcacgaggctgcttccctctgtttacgccattgtagcacgtgtgtagccctggtcat aaggggcatgatgatttgacgtcgtccccaccttcctccaggttatccctggcagtctctctagagtgcccacctnatatgctggctactaaagatagggggttgcgctcgttgcg ggacttaacccaacatctcacgacacgagctgacgacaaccatgcaccacctgtcactcctgtcccgaaggaaaggtccggttaaggaccggtcagaaggatgtcaaga ccaggtaaggttcttcgcgttgcttcgaattaaaccacatgctccaccgcttgtgcgggtccccgtcaattcctttgagtttcattcttgcgaacgtactccccaggtggaatactta ctgcgttggctgcggcaccgaagcctctacggccccgacacctagtattcatcgtttacggcgtggactaccagggtatctaatcctgtttgctccccacgctttcgtgcctcagt gtcagtttcagtccagtaagccgccttcgccactgatgttcctcctaatatctacgcatttcaccgctacactaggaattccgcttacctctcctgcactccagtctgacagtttcaa aagcagtcccagagttaagccctgggtttcacttctgacttgccataccacctacgcacccttacacccagtaattccggataacgcttgcccctacgtattaccgcggctg ctggcacgtagttagccgggggcttcttagtcaggtaccgtcattttcttccctgctgatagagctttacataccgagatacttctt

B                                                                    C

Firmicutes; Clostridia; Clostridiales; Lachnospiraceae; Anaerostipes

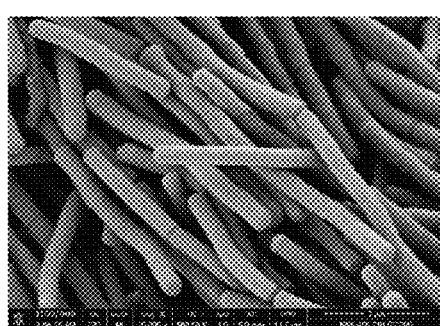

FIG. 1

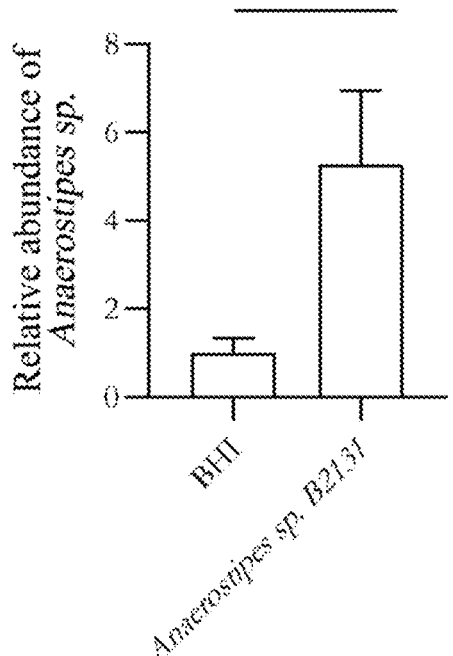
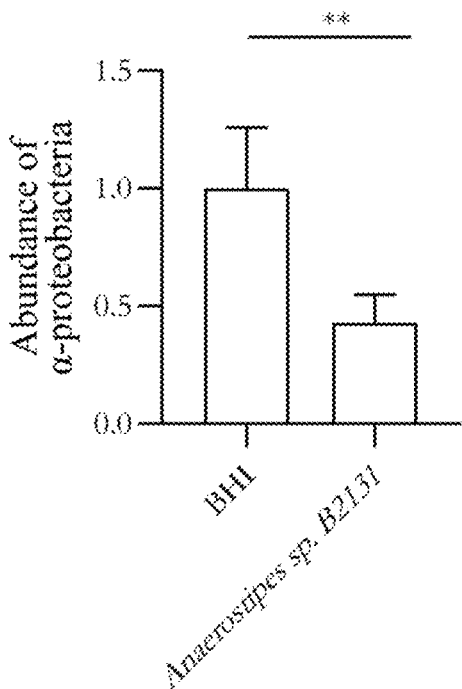
FIG. 3

ANAEROSTIPES SP B2131 STRAIN AND APPLICATION THEREOF IN INFLAMMATORY BOWEL DISEASES

REFERENCE TO SEQUENCE LISTING

The substitute sequence listing is submitted as an ASCII formatted text filed via EFS-Web, with a file name of "Substitute_Sequence_Listing. TXT", a creation date of Sep. 7, 2025 and a size of 2862 bytes. The substitute sequence Listing filed via EFS-Web is a part of the specification and is incorporated in its entirety by reference herein.

TECHNICAL FIELD

The present disclosure belongs to the technical field of microorganisms, specifically relates to an application of an *Anaerostipes* sp. strain in preventing and/or treating inflammatory bowel diseases.

BACKGROUND

Inflammatory bowel disease (IBD) is a class of diseases characterized by chronic inflammation of the digestive tract, mainly including subtypes of ulcerative colitis (UC) and Crohn's disease (CD). The clinical manifestations of IBD are mainly continuous diarrhea, abdominal pain, rectal bleeding/hematochezia, weight loss, etc., which seriously affect the patient's quality of life and are prone to relapse, so it is considered as a lifelong disease. As of 2016, the incidence of UC and CD in European and American countries exceeded 0.3% (affected population/country population), of which the incidence of UC was the highest in Norway, reaching 0.505%, and the incidence of CD in Germany was the highest in the world with 0.322%. At present, the incidence of IBD in developed countries has been at a plateau stage, and there is no obvious trend of improvement. Since 1990, the incidence in newly industrialized countries in Africa, Asia and South America is rising rapidly at a rate of 5-10% per year. With the significant changes in people's dietary structure, lifestyle and living environment, the incidence of IBD in China (currently 1.8 per 100,000 people) has shown a trend of sustained and rapid growth, and it has become a common disease of the digestive system. The understanding of the pathogenesis of IBD has developed from the initial adaptive immunity to the present natural immunity. A group of immune cells involved in the pathogenesis and the inflammatory mediators and cytokines secreted by them have been identified, and it is gradually recognized that the intestinal flora disorders, the innate immune system disorders and abnormal interactions between them play an important role in the occurrence and development of IBD. The pathogenesis of IBD can be summarized as: Genetic susceptibility and/or external environmental stimuli result in the disturbance of intestinal flora and the dysfunctions of the normal intestinal mucosal barrier, so that a large amount of intestinal microorganisms and their metabolites enter the intestinal wall through the broken barrier and activate the intestinal natural immune system, thus resulting in acute inflammation; If the body's autoimmune system is dysfunctional, it will not be able to control the damages to normal cells caused by acute inflammation and immune responses in time, and inflammation tends to become chronic, thus leading to the occurrence and development of fibrosis, atypical hyperplasia and even tumors.

The human intestine is a diversified and vibrant microecosystem. The latest research results show that there are more than 1,000 kinds of microorganisms in the human intestinal flora, with a total number of about $4 \times 10^{13}$, which is equivalent to the number of human cells. Although the intestinal flora is diverse and abundant, the dominant bacteria that account for 98% of the intestinal flora are from the phyla Bacteroidetes, Firmicutes, Proteobacteria and Actinobacteria. In recent years, the role of intestinal flora in the occurrence and development of IBD is getting more and more attention. The study has found that compared with the intestinal flora of healthy people, the intestinal flora of IBD patients has changed significantly, and the diversity of its species is significantly lower than that of healthy people. Among them, the diversity of symbiotic anaerobic bacteria Firmicutes and Bacteroidetes decreases significantly, while the diversity of Proteobacteria increases significantly. Analysis of flora composition showed that, the content of Lachnospiraceae in the feces of IBD patients was significantly reduced; while *Bifidobacterium breve* and *Clostridium symbiosum* were significantly enriched in UC patients, and 12 kinds of bacteria, including *Clostridium clostridioforme, Escherichia coli* and the like, increased specifically in CD patients. At the same time, in the Spanish IBD patient cohort study, it was found that 6 kinds of microorganisms, including *Faecalibacterium*, Peptostreptococcaceae and the like, were significantly reduced in the feces of CD patients, while *Fusobacterium* and *Escherichia* were significantly increased. In summary, a large number of clinical data indicated that the intestinal flora of IBD patients is seriously imbalanced.

Based on the fact that intestinal flora imbalance and intraluminal antigen stimulation are important reasons for the onset and recurrence of IBD, probiotics have been widely used in the past 10 years to improve the intestinal microenvironment, restore the body's normal flora, and reduce inflammation, so as to achieve the purposes of controlling the intestinal tract inflammation and maintaining remission, for example, Mesalazine combined with *Bifidobacterium* has achieved good results in the clinical treatment of IBD. The development of probiotics with different functions is considered to be an important way to prevent and treat IBD in the future. *Anaerostipes* is a genus of Firmicutes, Clostridia, Clostridiales, Lachnospiraceae. There have been some studies showing that some species of Lachnospiraceae have the effect of relieving enteritis, while the abundance of Lachnospiraceae in IBD patients is generally lower than that in normal people. However, up to now, there is still a lack of Lachnospiraceae species for the treatment of IBD, so it is of great significance to find and develop Lachnospiraceae strains.

The invention 2016800915239 "*Anaerostipes caccae* and application thereof" provides a use of *Anaerostipes caccae* in the treatment and/or prevention of inflammation-related diseases, and also provides a composition for treating and/or preventing inflammation-related diseases, including medicines, beverages, food, or animal feed compositions, and the like, as well as a method of improving mammalian intestinal pathology, slowing down the weight loss of mammals, and/or reducing the disease activity index (DAI) of mammals.

SUMMARY

The technical problem to be solved by the present disclosure is to provide an *Anaerostipes* sp. strain and an application thereof in preventing and/or treating an inflammatory bowel disease.

That is, the present disclosure provides an intestinal isolated bacterium, as a probiotic preparation, which is applied in a pharmaceutical composition, food, health care product, food additive and other products for regulating the homeostasis of intestinal flora, preventing and treating the the occurrence of intestinal diseases such as an inflammatory bowel disease.

To solve the above technical problem, the present disclosure provides an *Anaerostipes* sp. B2131 strain, which has a deposit number of CGMCC NO. 1.5295.

The present disclosure also provides an application of the above *Anaerostipes* sp. B2131 strain in the preparation of a medicine for preventing and/or treating an inflammatory bowel disease.

As an improvement of the application of the present disclosure: the medicine comprises a pharmaceutically effective dose of *Anaerostipes* sp. B2131 strain and a pharmaceutically acceptable carrier.

As a further improvement of the application of the present disclosure: the pharmaceutically effective dose is $10^6$-$10^{10}$ CFU.

As a further improvement of the application of the present disclosure: the pharmaceutically acceptable carrier is milk powder, lactose, cyclodextrin, maltose, glucose, glycerin, sodium glutamate, vitamin C, mannose, galactose, mannitol or methylcellulose.

As a further improvement of the application of the present disclosure: the inflammatory bowel disease is ulcerative colitis or Crohn's disease.

The present disclosure also provides a pharmaceutical composition for preventing and/or treating an inflammatory bowel disease, wherein the pharmaceutical composition comprises a pharmaceutically effective dose of *Anaerostipes* sp. B2131 strain which has a deposit number of CGMCC No. 1.5295.

As an improvement of the pharmaceutical composition of the present disclosure: the pharmaceutically effective dose is $10^6$-$10^{10}$ CFU.

The present disclosure also provides a food/health care product/food additive for preventing and/or treating an inflammatory bowel disease, wherein the food/health care product/food additive comprises an *Anaerostipes* sp. B2131 strain which has a deposit number of CGMCC No. 1.5295.

The present disclosure gets *Anaerostipes* sp. B2131 by separation from feces, of which the preservation information is as follows: the preservation name is *Anaerostipes* sp., Depository Authority: Common Microorganism Center of China Committee for Culture Collection of Microorganisms, Preservation address: No. 3, Courtyard 1, Beichen West Road, Chaoyang District, Beijing; Deposit No: CGMCC NO. 1.5295, Preservation time: Oct. 8, 2019.

The comparison result of 16S rDNA partial sequence of *Anaerostipes* sp. B2131 and the morphology of the bacteria observed by a scanning electron microscope are shown in FIG. 1.

The *Anaerostipes* sp. B2131 strain is capable of regulating the homeostasis of intestinal flora, preventing and treating intestinal diseases such as an inflammatory bowel disease. That is, it has the functions of inhibiting the growth of harmful intestinal bacteria and regulating the intestinal flora.

The present disclosure also provides a quantitative PCR method for detecting *Anaerostipes* sp. B2131 strain.

The present disclosure has found through detection that the content of *Anaerostipes* sp. B2131 strain in IBD patients decreased significantly.

The present disclosure proves that the *Anaerostipes* sp. B2131 strain has a good effect in preventing and/or treating an inflammatory bowel disease.

The present disclosure has confirmed through in vivo and in vitro related experiments that, *Anaerostipes* sp. B2131 strain can inhibit the growth of harmful intestinal bacteria, improve the intestinal flora, has excellent resistance to inflammatory bowel diseases, including ulcerative colitis or Crohn's disease, and has no toxic side effects, so it can be durably and effectively applied in the preparation of medicines, pharmaceutical compositions, food, health care products or food additives for preventing and/or treating inflammatory bowel diseases. These medicines, pharmaceutical compositions, food, health care products or food additives can be used for preventing and treating inflammatory bowel diseases, and have significant application value.

The *Anaerostipes* sp. B2131 strain of the present disclosure differs from *Anaerostipes* caccae strains. Firstly, the present disclosure has an experimental basis, that is, *Anaerostipes* sp. B2131 strain-specific PCR primers and fluorescent quantitative PCR technology are used to detect feces, and the results show that the content of this strain in IBD patients is significantly lower than that of the normal control group. The 16S rDNA sequence similarity between the *Anaerostipes* sp. B2131 strain of the present disclosure and *Anaerostipes* caccae is only 95% (being considered as the same species only when the similarity reaches 97%), indicating that the two strains are different species of the same genus, so there are some differences in their biological characteristics and functions. The research results show that, *Anaerostipes* sp. B2131 strain has the effect of regulating the intestinal flora, for example, it can significantly inhibit the intestinal harmful α-proteobacteria. In terms of the effect of treating enteritis, *Anaerostipes* sp. B2131 reduced the weight loss by about 10%, and the length of the intestine is about 1.3 cm longer than that of the control group. HE slices also show that the intestinal epithelium is more complete, and the expression of IL-6 and other inflammatory factors was significantly reduced, indicating that the *Anaerostipes* sp. B2131 strain is also better than *Anaerostipes* caccae strain in improving enteritis.

BRIEF DESCRIPTION OF THE DRAWINGS

The specific embodiments of the present disclosure will be described in further detail below in conjunction with the accompanying drawings.

FIG. 1 shows the identification results of *Anaerostipes* sp. B2131 strain; wherein, (A) shows the partial 16S rDNA sequence of *Anaerostipes* sp. B2131 strain;

(B) shows the phylogenetic classification results of the strain;

(C) shows the morphology of the bacteria observed under a scanning electron microscope.

Figure 2:
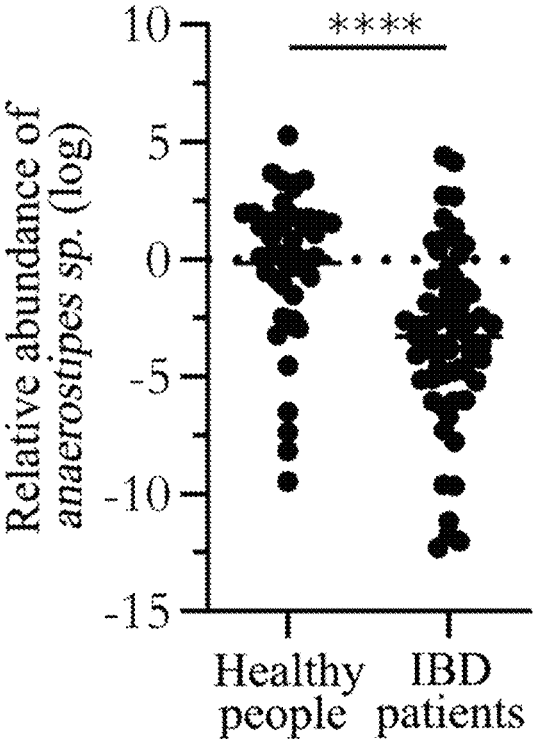

FIG. 2 shows the abundance detection of *Anaerostipes* sp. B2131 strain in the fecal flora of healthy controls and IBD patients.

FIG. 3 shows that *Anaerostipes* sp. B2131 strain can inhibit the growth of the harmful intestinal bacteria α-proteobacteria.

Figure 4:
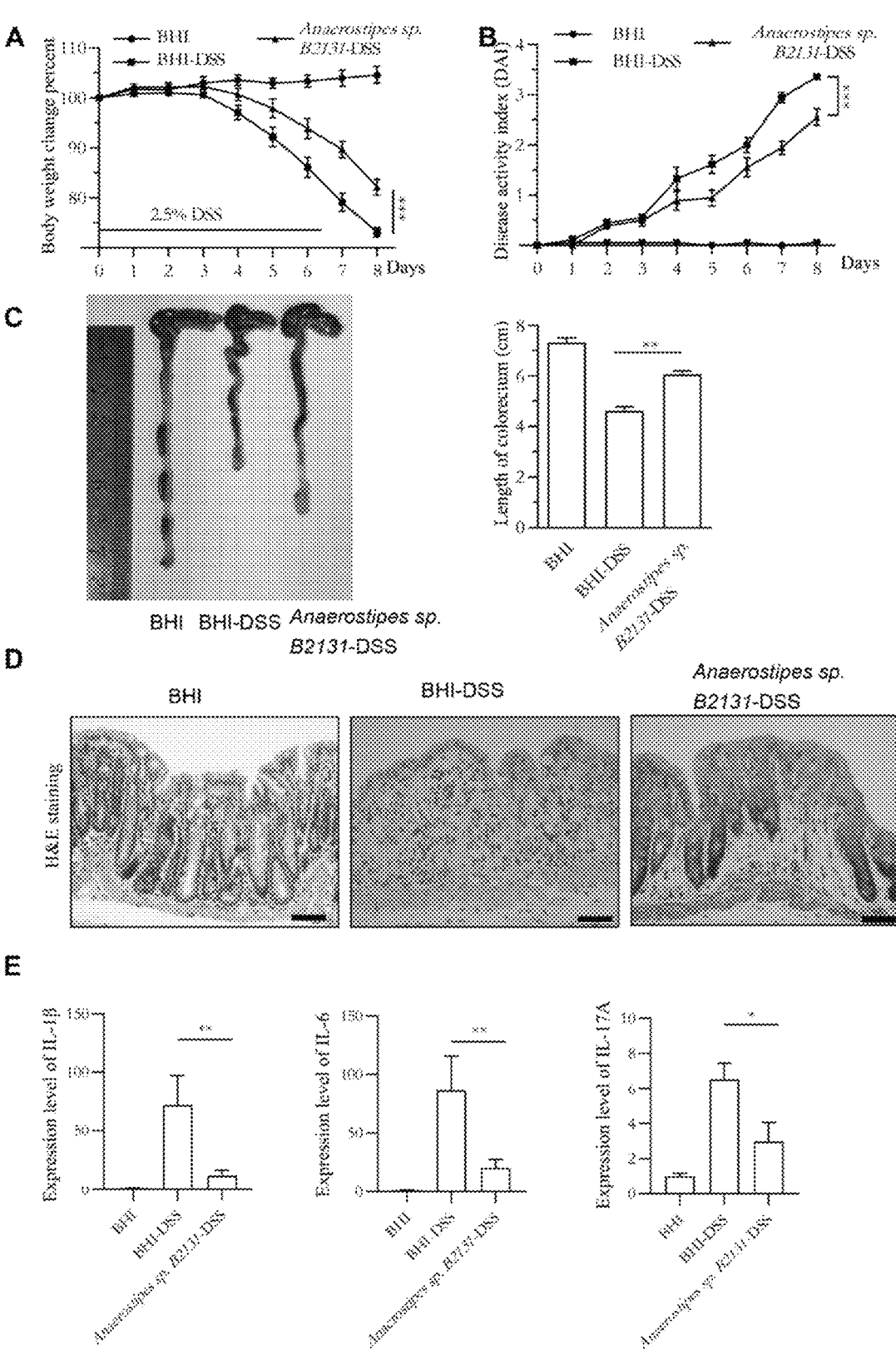

FIG. 4 shows that oral administration of *Anaerostipes* sp. B2131 strain can reduce the phenotype of enteritis induced by DSS in mice; wherein, (A) shows the body weight change curves of mice in the BHI control group, the BHI-DSS treatment group and the *Anaerostipes* sp. B2131-DSS treatment group during the DSS-induced ententis;

(B) shows the disease activity indexes of the three groups of mice during the DSS-induced enteritis;

(C) shows the length of the colorectum of the three groups of mice on the 9th day of the DSS-induced enteritis (the shorter the intestine, the more serious the enteritis);

(D) shows that distal colon H&E staining of the three groups of mice shows the destruction of the intestinal epithelium;

(E) shows the expression of inflammatory factors IL-1β, IL-6 and IL-17A in the colon tissue of the three groups of mice.

DETAILED DESCRIPTION OF THE EMBODIMENTS

The present disclosure will be further described below in conjunction with specific embodiments, but the protection scope of the present disclosure is not limited to this Reagents, Materials and Equipment

| Name | Manufacturer |
|---|---|
| PCR super MIX | Beijing TransGen Biotech Co., Ltd. |
| SYBR ® Premix Ex Taq ™ | Takara Bio Inc., Japan |
| BHI Culture solution | BD Difco Co., USA |
| L-cysteine | Shanghai Aladdin Biochemical Technology Co., Ltd. |
| Dextran sulfate sodium (DSS) | MP Co., Canada |
| C57/BL6 mice | Shanghai SLAC Laboratory Animal Co., Ltd. |
| Biochemical incubator | Ningbo Saifu Laboratory Instrument Factory |
| Anaerobic incubator | Shanghai Longyue Instrument Equipment Co., Ltd. |
| Clean bench | Suzhou Antai Air Tech Co., Ltd. |
| Quantitative PCR Instrument | Roche Co., USA |
| Scanning electron microscope | FEI Co., USA |

Embodiment 1. Isolation, Cultivation and Identification of *Anaerostipes* sp. B2131 Strain (1) Preparation of Conditioned Medium Pre-deoxygenated liquid BHI medium (containing 5% bovine serum and 0.1% cysteine): Weighing 37 g brain heart infusion (BD Co.) into a 1 L conical flask, adding 1 g cysteine and double distilled water to make the volume to 1000 ml, stirring to dissolve, and then sterilizing in an autoclave at 121° C. for 15 min; after sterilization, placing the medium into an anaerobic incubator, cooling to about 40-50° C., adding 50 ml fetal bovine serum and shaking evenly to obtain pre-deoxygenated liquid BHI medium, and then dispensing into 50 ml centrifuge tubes.

Pre-deoxygenated solid BHI medium (containing 5% bovine serum, 0.1% cysteine and 1 mg/L aztreonam): Weighing 37 g brain heart infusion (BD Co.) into a 1 L conical flask, adding 1 g cysteine, 15 g agar powder and double distilled water to make the volume to 1000 ml, stirring to dissolve, and then sterilizing in an autoclave at 121° C. for 15 min; after sterilization, placing the medium into an anaerobic incubator, cooling to about 40-50° C., adding 50 ml fetal bovine serum and 1 mg aztreonam and shaking evenly to obtain pre-deoxygenated solid BHI medium; then carrying out the inverted plate operation, adding 20-25 ml pre-deoxygenated solid BHI medium into each petri dish with a diameter of 10 cm, and letting it solidify by natural cooling.

(2) Sample Collection and Bacterial Culture

First, taking 0.1 g fresh healthy mouse feces into a 1.5 ml centrifuge tube, and promptly transferring into an anaerobic incubator, adding 1 ml pre-deoxygenated liquid BHI medium, stirring with a sterile pipette tip into a homogenate; then diluting the bacterial suspension 5 times in a gradient of 1/10 (diluting with the pre-deoxygenated liquid BHI medium as the solvent), spreading 100 µL on the pre-deoxygenated BHI solid plate (pre-deoxygenated solid BHI medium), placing into an anaerobic box and culturing at 37° C. for 72 h; picking a single clone and inoculating it onto a new BHI solid plate for subculture.

(3) Strain Identification

Picking a colony with a small pipette tip into a 1.5 ml centrifuge manifold, adding 20 µL double distilled water and heating in a boiling water bath for 5 min. Then performing colony PCR using 16S rDNA universal primers.

The primer sequences used are:

| Name | Sequence |
|---|---|
| F340 | ACTCCTACGGGAGGCAGCAGT (SEQ ID NO: 1) |
| R1492 | GGTTACCTTGTTACGACTT (SEQ ID NO: 2) |

The PCR reaction system is:

| Components | Volume (µL) |
|---|---|
| 2 × taq MIX | 10 |
| Upstream and downstream primers, each 10 µM | 1 |
| dd H$_2$O | 8 |
| Colony | 1 |
| Total volume | 20 |

The reaction procedures are:

| Step | Temperature (° C.) | Time (sec) |
|---|---|---|
| Predenaturation | 95 | 300 |
| Denaturation | 95 | 20 |
| Annealing | 58 | 30 |
| Extending | 72 | 60 |
| Back to denaturation step Cycle for 30 times | — | — |
| Continue extending | 72 | 300 |
| Cooling | 4 | Hold |

The obtained PCR products were then sent to a biotech company for sequencing, getting a sequence with a length of 1011 bp, as shown in FIG. 1A. The sequence was then compared in the NCBI or RDP database to obtain the species classification information, from which it can be confirmed as an *Anaerostipes* sp. species, as shown in FIG. 1B.

The obtained *Anaerostipes* sp. B2131 strain is preserved, of which the preservation information is as follows: the preservation name is *Anaerostipes* sp., Depository Authority: Common Microorganism Center of China Committee for Culture Collection of Microorganisms, Preservation address: No. 3, Courtyard 1, Beichen West Road, Chaoyang District, Beijing; Deposit No: CGMCC NO. 1.5295, Preservation time: Oct. 8, 2019.

(4) Observation on the Morphology of Bacteria Through a Scanning Electron Microscope First, an inoculated loop of colonies were selected in the anaerobic incubator and placed into 10 ml of pre-deoxygenated BHI liquid medium, and then placed in the anaerobic incubator at 37° C., and cultured overnight while standing to make the bacteria liquid turbid. Then, 1.5 ml of bacterial sample was taken and centrifuged at 4000 rpm for 5 min, the supernatant was discarded, and then washed once with PBS buffer. The samples were then resuspended with the fresh formulated glutaraldehyde (formulated with PBS buffer at PH=7.4) at a volume concentration of 2.5%, and fixed overnight at 4° C. After the fixation, the cells were collected by centrifugation at 4000 rpm for 5 min, the glutaraldehyde fixative was discarded, and the samples were washed 3 times with PBS buffer for 15 min each, and then 100 µl of 1% (mass %) osmic acid solution was added to fix the samples at room temperature for 1 h. Then the cells were collected by centrifugation at 4000 rpm for 5 min, the osmic acid fixative was discarded, and the samples were washed 3 times with PBS buffer for 15 min each. Then the samples were dehydrated with ethanol at a gradient of 30%, 50%, 70%, 80%, 90%, 95%, 100% respectively (for 15 min for each concentration). Finally, the samples were dried at critical point (a routine operation step in sample preparation for Cryo-electron microscope), and the samples were observed through a scanning electron microscope. The bacteria morphology observed through the scanning electron microscope was shown in FIG. 1C.

In summary, monoclonal strains were isolated from the feces of healthy mice, and the bacteria were identified through 16S rDNA sequence alignment as species of Bacteria, Firmicutes, Clostridia, Clostridiales, Lachnospiraceae, *Anaerostipes* sp.; the scanning electron microscope image shows that *Anaerostipes* sp. B2131 strain has a morphology of long *bacillus*, no flagella, and smooth cell wall.

Embodiment 2. Abundance Detection of *Anaerostipes* sp. Stain Content in IBD Patients and Healthy Controls
(1) Fecal Flora DNA Extraction Fecal samples of IBD patients were provided by inpatients at the Inflammatory Bowel Disease Center of Sir Run Run Shaw Hospital, Zhejiang University. After the samples were collected, they were frozen and stored in a refrigerator at −20° C. in time, and transported while being frozen on dry ice to a refrigerator at −80° C. in the laboratory within 2 days for preservation. Fecal samples of healthy people were provided by healthy physical examinees, and taken back to the laboratory and stored in a refrigerator at −80° C. within 5 hours. When extracting fecal DNA, the samples were taken out from −80° C., from which 100-150 mg of feces was taken with a medicine spoon into a 1.5 ml centrifuge tube without thawing; then, a fecal flora DNA extraction kit (Qiagen) was employed to extract the total fecal flora DNA, and then the concentration, purity and quality of DNA were detected using a Nanodrop 2000 ultraviolet microspectrophotometer and agarose gel electrophoresis, and the follow-up operations were performed after passing the quality inspection.
(2) Detection of the Content of *Anaerostipes* sp. Strain in the Samples by the Quantitative PCR Method The above fecal flora DNA was diluted to 10 ng/µl, then added into a 384-well plate, and detected quantitatively with a Roche 480II system.

The primer sequences are:

| Name | Sequence |
|---|---|
| Universal bacterial F | ACTCCTACGGGAGGCAGCAGT_ (SEQ ID NO: 3) |
| Universal bacterial R | ATTACCGCGGCTGCTGGC (SEQ ID NO: 4) |
| Anaerostipes F | GTGAGTGAAGAAGTATTTCG (SEQ ID NO: 5) |
| Anaerostipes R | GCTTTCACTTCTGACTTACC (SEQ ID NO: 6) |

The PCR reaction system is:

| Components | Volume (µL) |
|---|---|
| 2 × SYBR Green | 3 |
| Upstream and downstream primers, each 1 µM | 1 |
| dd H$_2$O | 1 |
| DNA | 1 |
| Total volume | 6 |

The reaction procedures are:

| Step | Temperature (° C.) | Time (sec) |
|---|---|---|
| Denaturation | 95 | 30 |
| Cycling | 95 | 5 |
| (45 times) | 60 | 30 |
| Cooling | 50 | 15 |

All the samples were subjected to three parallel tests. With Universal bacteria as the internal reference, the relative abundance of *Anaerostipes* sp. strain in each sample was calculated by the $2^{-\Delta\Delta Ct}$ method.

The results were shown in FIG. 2. It can be concluded from FIG. 2 that, the imbalance of intestinal flora is closely related to the occurrence and development of IBD, and the content of *Anaerostipes* sp. strain in the intestine of IBD patients is significantly lower than that of healthy people.

Embodiment 3. Cultivation of *Anaerostipes* sp. B2131 Strain and Detection of Butyric Acid Production Capacity (1) Culture of *Anaerostipes* sp. B2131 Strain (Anaerobic Culture)

The *Anaerostipes* sp. B2131 strain, with a deposit number of CGMCC NO. 1.5295, was cultured anaerobically in pre-deoxygenated liquid BHI medium at 37° C. (the culture time was about 48 hours), until the colony grew to a diameter of 1-2 mm. Then one colony was picked with a pipette into 15 ml pre-deoxygenated liquid BHI medium, and cultured anaerobically at 37° C. for 48 hours while standing, to obtain the *Anaerostipes* sp. B2131 strain solution, of which the density was about 5×10$^8$ CFU/mL.
(2) Detection of Butyric Acid Production Capacity of *Anaerostipes* sp. B2131 Strain 1 ml of the *Anaerostipes* sp. B2131 strain solution was taken and centrifuged at 12000 r/min for 5 min. The supernatant was taken, diluted 1000 times with double distilled water, and adjusted to pH 2-3 with hydrochloric acid solution, and mixed well by vortex shaking; and then centrifuged at 12000 r/min for 10 min. The supernatant was collected carefully into a chromatographic bottle. At the same time, standard butyric acid solutions of 10 μg/mL, 50 μg/mL, 100 μg/mL, 200 μg/mL, 500 μg/mL and 1000 μg/mL were formulated. After then, the samples were analyzed using Agilent 6890N gas chromatograph in conjuction with a gas chromatographic column DB-624UI: 1 μL of sample was taken into the injection hole, the initial column temperature was 100° C., the carrier gas was high-purity nitrogen, the flow rate was 1.1 mL/min, holding for 3 minutes; then the temperature was elevated to 200° C. at a rate of 10° C./min for 3 min; finally, a standard curve was drawn based on the area under the curve of standard butyric acid solution, and the concentration of butyric acid in the strain solution was calculated based on the area under the curve of the sample butyric acid. It was determined that under the condition of pre-deoxygenated BHI medium, the butyric acid production of *Anaerostipes* sp. B2131 strain at 48 hour was 41.3 mmol/L.

Embodiment 4. *Anaerostipes* sp. B2131 Strain Inhibits the Growth of Harmful Intestinal Bacteria α-Proteobacteria (1) Preparation of WT Mice 14 8-week-old wild-type BL/C57 mice were firstly purchased from Shanghai SLAC Co. and kept in the SPF barrier system of the Laboratory Animal Center of Zhejiang University. After adaptation for one week, the mice were randomly divided into a BHI solvent control group and a *Anaerostipes* sp. B2131 strain treatment group, with 7 mice in each group.

(2) Intestinal Colonization of *Anaerostipes* sp. B2131 Strain.

The *Anaerostipes* sp. B2131 strain solution cultured in Embodiment 3 was taken and centrifuged at 4000 rpm for 5 min to collect the bacterial cells. The bacteria were then resuspended in pre-deoxygenated liquid BHI medium to a final concentration of about $10^9$ CFU/ml. WT mice were treated by intragastric administration at a dose of 200 μL *Anaerostipes* sp. B2131 per mouse every other day for 2 weeks. At the same time, the control group was only gavaged with the pre-deoxygenated liquid BHI medium.

(3) Quantitative detection of the abundance of *Anaerostipes* sp. B2131 strain and the abundance of α-proteobacteria. On day 7 after the completion of the gavage treatment, the feces of mice was collected, the fecal flora DNA was extracted according to the method described in the above Embodiment 2 and detected by the quantitative PCR.

The results were shown in FIG. 3, from which it can be concluded that, *Anaerostipes* sp. B2131 strain can regulate the intestinal flora, for example, significantly reduce the abundance of the harmful intestinal bacteria α-proteobacteria.

Embodiment 5. *Anaerostipes* sp. B2131 Strain can Alleviate the Phenotype of DSS-Induced Enteritis in Mice (1) Preparation of WT Mice 30 8-week-old wild-type BL/C57 mice were purchased from Shanghai SLAC Co. and kept in the SPF barrier system of the Laboratory Animal Center of Zhejiang University. After adaptation for one week, the mice were randomly divided into three groups, a BHI control group, a BHI-DSS group and an *Anaerostipes* sp. B2131-DSS group respectively.

(2) Intestinal Colonization of *Anaerostipes* sp. B2131 Strain;

The *Anaerostipes* sp. B2131 strain solution cultured in Embodiment 3 was taken and centrifuged at 4000 rpm for 5 min to collect the bacterial cells. The bacteria were then resuspended in pre-deoxygenated liquid BHI medium to a final concentration of about $10^9$ CFU/ml. WT mice were treated by intragastric administration at a dose of 200 μL *Anaerostipes* sp. B2131 per mouse every other day for 2 weeks. At the same time, the BHI group and the BHI-DSS group were only gavaged with the pre-deoxygenated liquid BHI medium. After the 2-week gavage treatment is over, the mice can be tested for inducing enteritis.

(3) Establishment of Mice DSS-Induced Enteritis Model

The drinking water for mice in the BHI-DSS group and the *Anaerostipes* sp. B2131-DSS group was replaced with a DSS aqueous solution of 2.5% (mass %). After 7 days of treatment, it returned to regular drinking water until the end of the experiment. That is, on days 1-7 of DSS-induced enteritis, the mice in the BHI-DSS group and the *Anaerostipes* sp. B2131-DSS groups drank a DSS aqueous solution of 2.5%, and they drank the regular drinking water on the 8-9th days; while mice in the BHI control group always drank the regular drinking water during the 9 days.

From days 1 to 9 of enteritis induction, the change of body weight, the dryness of stool, and the hematochezia profile were recorded. Body weight scores: 0, no weight loss; 1, reduced by 1-5%; 2, reduced by 6-10%; 3, reduced by 11-20%; 4, reduced over 20%. Stool scores: 0, solid stool; 1, solid stool, easy to deform; 2, unshaped stool; 3, liquid stool. Hematochezia scores: 0, negative in occult blood test; 1, positive in occult blood test; 2, visible blood in the stool; 3, serious hematochezia. The disease active index (DAI) is the average of body weight, stool and hematochezia scores. The comparison of the body weight changes was shown in FIG. 4A, and the comparison of the disease active indexes was shown in FIG. 4B.

It can be known from the figures that, mice in the BHI-DSS group and the *Anaerostipes* sp. B2131-DSS group showed enteritis phenotypes of weight loss and increased disease active index after drinking DSS, indicating that the DSS enteritis induction was successful. Upon further comparison, the extent of weight loss of *Anaerostipes* sp. B2131-DSS mice was significantly less than that of the BHI-DSS group; at the same time, the disease active index of *Anaerostipes* sp. B2131-DSS mice was significantly lower than that of the BHI-DSS group, indicating that the symptoms of enteritis in mice with *Anaerostipes* sp. B2131 strain gavage were significantly improved compared with mice in the BHI-DSS group.

(4) On day 9 of DSS treatment, mice were killed by cervical dislocation. The colon was taken out of mice and measured for its length, with the results shown in FIG. 4C. About 1 cm of distal colon tissue segment was taken for Formalin fixation, and subsequently subjected to HE staining and histomorphological analysis, with the results shown in FIG. 4D. At the same time, about 1 cm of intestinal segment was taken to extract RNA, which was detected by the fluorescence quantitative PCR method for the expression of inflammatory factors, with the results shown in FIG. 4E.

According to FIG. 4C, it can be known that, in the DSS-induced enteritis model, the intestinal length (5.6 cm±0.8) of *Anaerostipes* sp. B2131-DSS mice was significantly longer than that of BHI-DSS mice (4.3 cm±0.5). According to FIG. 4D, it can be known that, there were still relatively complete crypt structures that can be seen on the intestinal epithelial cells of *Anaerostipes* sp. B2131-DSS mice, while the intestinal epithelium of BHI-DSS mice was completely destroyed, and there were no complete crypt structures. According to FIG. 4E, it can be known that, the expression levels of inflammatory factors IL-1β, IL-6 and IL-17A of *Anaerostipes* sp. B2131-DSS mice were significantly lower than that in the BHI-DSS group. This figure shows that both histomorphology and inflammatory factors reflect that the incidence of enteritis in *Anaerostipes* sp. B2131-DSS mice is significantly reduced.

Comparative embodiment. The *Anaerostipes* caccae in the Invention 2016800915239 *"Anaerostipes* caccae and application thereof"* was detected according to the above method described in the present disclosure, with the results compared with the present disclosure as follows:

First, the capacity to produce a beneficial short-chain fatty acid-butyric acid of *Anaerostipes* sp. B2131 after 48 hours was higher than that of *Anaerostipes* caccae by about 10%;

Second, *Anaerostipes* sp. B2131 has the function of regulating and improving the intestinal flora, while there was no data showing that *Anaerostipes* caccae has such a function;

Finally, in terms of the effect of protecting enteritis, *Anaerostipes* sp. B2131 is significantly better than *Anaerostipes* caccae in improving the extent of enteritis. The Specifically, on day 7 of DSS-induced enteritis, the weight loss of *Anaerostipes* sp. B2131-DSS group was 9.1% less than that of the BHI-DSS group (however, when calculated according to the body weight improvement data of the *Anaerostipes caccae* AF04-45 treatment group, the result of (Body weight of AF05-45 group on day 7-Body weight of model group on day 7)/Body weight of AF04-45 group on day 1) was only 6.8%), the length of the intestine increased by 1.45 cm (however, the intestinal length difference between the *Anaerostipes* caccae AF04-45 group and the model group was 1.19 cm); in addition, the intestinal epithelium was more complete, and the expression of inflammatory factors was significantly reduced.

Finally, it should be noted that the above-listed are only a few specific embodiments of the present disclosure. Obviously, the present disclosure is not limited to the above embodiments, and many variations are possible. All variations that can be directly derived or associated by a person of ordinary skills in the art from the content of the present disclosure should be regarded as the protection scope of the present disclosure.

---

What is claimed is:

1. A method of preparing an *Anaerostipes* sp. B2131 strain in the preparation of a medicine for treating ulcerative colitis or Crohn's disease, the *Anaerostipes* sp. B2131 strain, which is deposited at Common Microorganism Center of China Committee for Culture Collection of Microorganisms (CGMCC) under deposit number 1.5295, and has a 16S rRNA gene sequence as shown in SEQ ID NO: 7, wherein the *Anaerostipes* sp. B2131 strain is prepared through the following steps:

(1) collecting fresh feces from a healthy mouse and adding the feces to a pre-deoxygenated liquid BHI medium which containing 5% bovine serum and 0.1% cysteine, followed by agitation to obtain a bacterial suspension;

(2) serially diluting the bacterial suspension with the pre-deoxygenated liquid BHI medium at a 1:10 gradient for five times to obtain a diluted suspension, plating 100 μL of the diluted suspension onto a pre-deoxygenated solid BHI plate including a pre-deoxygenated solid BHI medium which containing 5% bovine serum, 0.1% cysteine and 1 mg/L aztreonam, and placing the pre-deoxygenated solid BHI plate in an anaerobic chamber for incubation at 37° C. for 72 hours;

(3) picking a single colony from the pre-deoxygenated solid BHI medium and inoculating the single colony onto another pre-deoxygenated solid BHI medium for subculturing; and (4) transferring one colony into 20 μL of double-distilled water to form a mixture, boiling the mixture in a water bath for 5 minutes, and performing colony PCR using 16S rDNA universal primers to obtain a *Anaerostipes* species strain, with the 16S rDNA universal primers is as shown in SEQ ID NO: 1 and SEQ ID NO:2.

2. The method according to claim 1, wherein the medicine comprises a pharmaceutically effective dose of *Anaerostipes* sp. B2131 strain and a pharmaceutically acceptable carrier.

3. The method according to claim 2, wherein the medicine is provided to a subject and the pharmaceutically effective dose is $10^6$-$10^{10}$ Colony-Forming Unit/ml (CFU/ml).

4. The method according to claim 2, wherein the pharmaceutically acceptable carrier is milk powder, lactose, cyclodextrin, maltose, glucose, glycerin, sodium glutamate, vitamin C, mannose, galactose, mannitol or methylcellulose.

5. The method of claim 1, wherein the pre-deoxygenated liquid BHI medium is prepared by: adding cysteine and double-distilled water to a brain heart infusion, and stirring to obtain a first brain heart infusion mixture; then sterilizing the first brain heart infusion mixture at 121° C. under high pressure for 15 minutes; after sterilization, placing the first brain heart infusion mixture into an anaerobic incubator, cooling to about 40-50° C. to obtain a cooled mixture, adding fetal bovine serum to the cooled mixture and shaking to obtain the pre-deoxygenated liquid BHI medium.

6. The method of claim 1, wherein the pre-deoxygenated solid BHI medium is prepared by: adding cysteine, agar powder, and double-distilled water to a brain heart infusion, and stirring to obtain a second brain heart infusion mixture; then sterilizing the second brain heart infusion mixture at 121° C. under high pressure for 15 minutes; after sterilization, placing the second brain heart infusion mixture into an anaerobic incubator, cooling to about 40-50° C. to obtain a cooled mixture, adding fetal bovine serum and aztreonam to the cooled mixture and shaking to obtain the pre-deoxygenated solid BHI medium.

7. A pharmaceutical composition for regulating the intestinal flora, treating ulcerative colitis or Crohn's disease, wherein the pharmaceutical composition comprises es a pharmaceutically effective dose of *Anaerostipes* sp. B2131 strain with a deposit number of CGMCC No. 1.5295, and has a 16S rRNA gene sequence as shown in SEQ ID NO: 7, and a pharmaceutically acceptable carrier selected from the group consisting of milk powder, lactose, cyclodextrin, maltose, glucose, glycerin, sodium glutamate, vitamin C, mannose, galactose, mannitol, and methylcellulose, wherein the *Anaerostipes* sp. B2131 strain is prepared through the following steps:

(1) collecting fresh feces from a healthy mouse and adding the feces to a pre-deoxygenated liquid BHI medium, followed by agitation to obtain a bacterial suspension;

(2) serially diluting the bacterial suspension with the pre-deoxygenated liquid BHI medium at a 1:10 gradient for five times to obtain a diluted suspension, plating 100 μL of the diluted suspension onto a pre-deoxygenated solid BHI plate including a pre-deoxygenated solid BHI medium, and placing the pre-deoxygenated solid BHI plate in an anaerobic chamber for incubation at 37° C. for 72 hours;

(3) picking a single colony from the pre-deoxygenated solid BHI medium and inoculating the single colony onto another pre-deoxygenated solid BHI medium for subculturing; and (4) transferring one colony into 20 μL of double-distilled water to form a mixture, boiling the mixture in a water bath for 5 minutes, and performing colony PCR using 16S rDNA universal primers to obtain a *Anaerostipes* species strain, with the 16S rDNA universal primers is as shown in SEQ ID NO: 1 and SEQ ID NO:2.

8. The pharmaceutical composition according to claim 7, wherein providing the pharmaceutical composition to a subject and the pharmaceutically effective dose is $10^6$-$10^{10}$ CFU/ml.

9. The pharmaceutical composition of claim 7, wherein the pre-deoxygenated liquid BHI medium is prepared by: adding cysteine and double-distilled water to a brain heart infusion, and stirring to obtain a first brain heart infusion mixture; then sterilizing the first brain heart infusion mixture at 121° C. under high pressure for 15 minutes; after sterilization, placing the first brain heart infusion mixture into an anaerobic incubator, cooling to about 40-50° C. to obtain a cooled mixture, adding fetal bovine serum to the cooled mixture and shaking to obtain the pre-deoxygenated liquid BHI medium.

10. The pharmaceutical composition of claim 7, wherein the pre-deoxygenated solid BHI medium is prepared by: adding cysteine, agar powder, and double-distilled water to a brain heart infusion, and stirring to obtain a second brain heart infusion mixture; then sterilizing the second brain heart infusion mixture at 121° C. under high pressure for 15 minutes; after sterilization, placing the second brain heart infusion mixture into an anaerobic incubator, cooling to about 40-50° C. to obtain a cooled mixture, adding fetal bovine serum and aztreonam to the cooled mixture and shaking to obtain the pre-deoxygenated solid BHI medium.

11. A food/health care product/food additive for treating ulcerative colitis or Crohn's disease, wherein the food/health care product/food additive comprises a *Anaerostipes* sp. B2131 strain with a deposit number of CGMCC No. 1.5295, and has a 16S rRNA gene sequence as shown in SEQ ID NO: 7, wherein the *Anaerostipes* sp. B2131 strain is prepared through the following steps:

(1) collecting fresh feces from a healthy mouse and adding the feces to a pre-deoxygenated liquid BHI medium, followed by agitation to obtain a bacterial suspension;

(2) serially diluting the bacterial suspension with the pre-deoxygenated liquid BHI medium at a 1:10 gradient for five times to obtain a diluted suspension, plating 100 μL of the diluted suspension onto a pre-deoxygenated solid BHI plate including a pre-deoxygenated solid BHI medium, and placing the pre-deoxygenated solid BHI plate in an anaerobic chamber for incubation at 37° C. for 72 hours;

(3) picking a single colony from the pre-deoxygenated solid BHI medium and inoculating the single colony onto another pre-deoxygenated solid BHI medium for subculturing; and (4) transferring one colony into 20 μL of double-distilled water to form a mixture, boiling the mixture in a water bath for 5 minutes, and performing colony PCR using 16S rDNA universal primers to obtain a *Anaerostipes* species strain; and wherein the food/health care product/food additive further comprises a carrier selected from the group consisting of milk powder, lactose, cyclodextrin, maltose, glucose, glycerin, sodium glutamate, vitamin C, mannose, galactose, mannitol, and methylcellulose.

12. The food/health care product/food additive of claim 11, wherein the pre-deoxygenated liquid BHI medium is prepared by: adding cysteine and double-distilled water to a brain heart infusion, and stirring to obtain a first brain heart infusion mixture; then sterilizing the first brain heart infusion mixture at 121° C. under high pressure for 15 minutes; after sterilization, placing the first brain heart infusion mixture into an anaerobic incubator, cooling to about 40-50° C. to obtain a cooled mixture, adding fetal bovine serum to the cooled mixture and shaking to obtain the pre-deoxygenated liquid BHI medium.

13. The food/health care product/food additive of claim 11, wherein the pre-deoxygenated solid BHI medium is prepared by: adding cysteine, agar powder, and double-distilled water to a brain heart infusion, and stirring to obtain a second brain heart infusion mixture; then sterilizing the second brain heart infusion mixture at 121° C. under high pressure for 15 minutes; after sterilization, placing the second brain heart infusion mixture into an anaerobic incubator, cooling to about 40-50° C. to obtain a cooled mixture, adding fetal bovine serum and aztreonam to the cooled mixture and shaking to obtain the pre-deoxygenated solid BHI medium.

* * * * *

SEQUENCE LISTING

```
<160> NUMBER OF SEQ ID NOS: 7

<210> SEQ ID NO 1
<211> LENGTH: 21
<212> TYPE: DNA
<213> ORGANISM: Artificial Sequence
<220> FEATURE:
<223> OTHER INFORMATION: universal primers

<400> SEQUENCE: 1
actcctacgg gaggcagcag t                                              21

<210> SEQ ID NO 2
<211> LENGTH: 19
<212> TYPE: DNA
<213> ORGANISM: Artificial Sequence
<220> FEATURE:
<223> OTHER INFORMATION: universal primers

<400> SEQUENCE: 2
ggttaccttg ttacgactt                                                 19

<210> SEQ ID NO 3
<211> LENGTH: 21
<212> TYPE: DNA
<213> ORGANISM: Artificial Sequence
<220> FEATURE:
<223> OTHER INFORMATION: primers

<400> SEQUENCE: 3
actcctacgg gaggcagcag t                                              21

<210> SEQ ID NO 4
<211> LENGTH: 18
<212> TYPE: DNA
<213> ORGANISM: Artificial Sequence
<220> FEATURE:
<223> OTHER INFORMATION: primers

<400> SEQUENCE: 4
attaccgcgg ctgctggc                                                  18
```

-continued

```
<210> SEQ ID NO 5
<211> LENGTH: 20
<212> TYPE: DNA
<213> ORGANISM: Artificial Sequence
<220> FEATURE:
<223> OTHER INFORMATION: primers

<400> SEQUENCE: 5
gtgagtgaag aagtatttcg                                               20

<210> SEQ ID NO 6
<211> LENGTH: 20
<212> TYPE: DNA
<213> ORGANISM: Artificial Sequence
<220> FEATURE:
<223> OTHER INFORMATION: primers

<400> SEQUENCE: 6
gctttcactt ctgacttacc                                               20

<210> SEQ ID NO 7
<211> LENGTH: 1011
<212> TYPE: DNA
<213> ORGANISM: Anerostipes sp.
<220> FEATURE:
<221> NAME/KEY: misc_feature
<222> LOCATION: (310)..(310)
<223> OTHER INFORMATION: n is a, c, g, or t

<400> SEQUENCE: 7
tgggtcactg acttcgggcg ttactgactc ccatggtgtg acgggcggtg tgtacaagac     60
ccgggaacgt attcaccgcg acattctgat tcgcgattac tagcgattcc agcttcatgt    120
agtcgagttg cagactacaa tccgaactga gacgttattt ttgggatttg ctcactctca    180
cgaggctgct tccctctgtt tacgccattg tagcacgtgt gtagccctgg tcataagggg    240
catgatgatt tgacgtcgtc cccaccttcc tccaggttat ccctggcagt ctctctagag    300
tgcccacctn atatgctggc tactaaagat aggggttgcg ctcgttgcgg gacttaaccc    360
aacatctcac gacacgagct gacgacaacc atgcaccacc tgtcactcct gtcccgaagg    420
aaaggtccgg ttaaggaccg gtcagaagga tgtcaagacc aggtaaggtt cttcgcgttg    480
cttcgaatta aaccacatgc tccaccgctt gtgcgggtcc ccgtcaattc ctttgagttt    540
cattcttgcg aacgtactcc ccaggtggaa tacttactgc gttggctgcg gcaccgaagc    600
ctctacggcc ccgacaccta gtattcatcg tttacggcgt ggactaccag ggtatctaat    660
cctgtttgct ccccacgctt tcgtgcctca gtgtcagttt cagtccagta agccgccttc    720
gccactgatg ttcctcctaa tatctacgca tttcaccgct acactaggaa ttccgcttac    780
ctctcctgca ctccagtctg acagtttcaa aagcagtccc agagttaagc cctgggtttt    840
cacttctgac ttgccatacc acctacgcac cctttacacc cagtaattcc ggataacgct    900
tgccccctac gtattaccgc ggctgctggc acgtagttag ccggggcttc ttagtcaggt    960
accgtcattt tcttccctgc tgatagagct ttacataccg agatacttct t            1011
```